（12）United States Patent
Morgan

(10) Patent No.: US 6,229,870 B1
(45) Date of Patent: May 8, 2001

(54) MULTIPLE FAN BEAM COMPUTED TOMOGRAPHY SYSTEM

(75) Inventor: Hugh T. Morgan, Highland Heights, OH (US)

(73) Assignee: Picker International, Inc., Highland Heights, OH (US)

( * ) Notice: Subject to any disclaimer, the term of this patent is extended or adjusted under 35 U.S.C. 154(b) by 0 days.

(21) Appl. No.: 09/199,733

(22) Filed: Nov. 25, 1998

(51) Int. Cl.$^7$ .................................................. G01N 23/00
(52) U.S. Cl. ............................................ 378/9; 378/4
(58) Field of Search ............................................ 378/4, 9

(56) References Cited

U.S. PATENT DOCUMENTS

| | | | |
|---|---|---|---|
| 4,250,425 | * | 2/1981 | Gaffay et al. ............................ 378/4 |
| 5,200,985 | | 4/1993 | Miller . |
| 5,241,577 | | 8/1993 | Burke et al. . |
| 5,268,955 | | 12/1993 | Burke et al. . |
| 5,274,690 | | 12/1993 | Burke et al. . |
| 5,291,538 | | 3/1994 | Burke et al. . |
| 5,305,363 | | 4/1994 | Burke et al. . |
| 5,335,255 | * | 8/1994 | Seppi ...................................... 378/4 |
| 5,467,377 | * | 11/1995 | Dawson .................................. 378/4 |
| 5,485,493 | | 1/1996 | Heuscher et al. . |
| 5,592,523 | | 1/1997 | Tuy et al. . |
| 5,712,889 | * | 1/1998 | Lanzara et al. ........................ 378/4 |
| 5,966,422 | * | 10/1999 | Dafni et al. ............................. 378/9 |

* cited by examiner

*Primary Examiner*—Craig E. Church
(74) *Attorney, Agent, or Firm*—Fay, Sharpe, Fagan, Minnich & McKee, LLP

(57) ABSTRACT

A CT scanner includes a stationary gantry (A) defining an examination region (12) and a rotating gantry (C) which rotates about the examination region. Multiple fan beam generators (B), each capable of producing a beam of radiation directed through the examination region, are mounted to the rotating gantry. The radiation beams are collimated (42) into a plurality of parallel thin fan shaped beams ($30_1$, $30_2$, ... $30_n$) that are projected through the examination region. X-rays are detected by at least an arc of x-ray detectors (14) or a plurality of parallel rings of detectors ($14_1$, $14_2$, ... $14_n$). The detectors generate signals indicative of the radiation received which are processed by a reconstruction processor (18) into a volumetric image representation for display on a monitor (20). In one embodiment, the signals are reconstructed into a series of spaced parallel slices. The object is indexed and additional slices are collected and reconstructed between previously reconstructed slices. In another embodiment, the region of interest moves such that each beam traverses a spiral path spanning one of a plurality of contiguous slabs. The multiple fan beam generators may be contained within a single elongated x-ray tube (40). Alternatively, the multiple fan beams can be generated by a plurality of angularly displaced x-ray tubes.

20 Claims, 7 Drawing Sheets

MULTIPLE FAN BEAM COMPUTED TOMOGRAPHY SYSTEM

BACKGROUND OF THE INVENTION

The present invention relates to the diagnostic imaging arts. The invention finds particular application in conjunction with volume CT imaging for medical purposes and will be described with particular reference thereto. However, it is to be appreciated that the present invention will also find application in conjunction with industrial, security, and other types of volume imaging apparatus and techniques.

In diagnostic imaging with CT scanners, a thin, fan shaped beam of radiation is projected from an x-ray source through a region of interest. The radiation source is rotated about the region of interest such that the same thin slice of the region of interest is irradiated from a multiplicity of directions spanning 360°. In a third generation scanner, an arc of radiation detectors is mounted to the same gantry as the radiation source such that the two rotate together. In a fourth generation scanner, the x-ray detectors are mounted stationarily in a ring 360° around the subject.

To image a volume of interest, a single slice image is typically generated. After a first slice image is generated, a subject support is indexed by a slice width generally on the order of a few millimeters, and another slice is generated. This slice image and index technique is repeated until slices spanning the volume of interest are generated. One drawback to this type of imaging is the relatively long time necessary to generate a large plurality of slices. Because the first and last slice are taken at a significantly different time, the volume image is distorted by a time evolution of the region of interest.

In spiral scanning techniques, the patient is generally moved continuously through the x-ray beam as the x-ray source rotates around the region of interest. In this manner, the fan shaped beam of radiation and the region of interest move in a spiral pattern relative to each other. The continuous motion is faster than indexing between slices, but still relatively slow.

In order to reduce the imaging time, some scanners collimate the beam of radiation into two slices. When the beam of radiation is collimated into two slices, two sets of radiation detectors disposed end to end are commonly provided. Typically, the thickness of the irradiated slice and the spacing between slices are adjustable. Such adjustments are relatively straight forward for two beams of radiation. However, the requirement that each beam of radiation strike only a single set of radiation detectors renders collimation into more than two beams mechanically awkward. Moreover, because the two beams originate from a common focal point, they are divergent, not parallel to each other. The divergent rays complicate and introduce errors into reconstruction techniques in which data is reconstructed into parallel slices. Moreover, as radiation from a single source is collimated into more beams, such beams become more widely divergent.

Systems have been proposed for examining the region of interest with a cone beam of radiation. However, cone beam image reconstruction is computationally intensive and slow. Moreover, cone beam imaging has a fixed resolution, based on detector size. Further, cone beam reconstructions tend to suffer from insufficiency of data problems, image artifacts, and other reconstruction errors.

The present invention contemplates a new, improved CT system which overcomes the above difficulties and others.

BRIEF SUMMARY OF THE INVENTION

In accordance with the present invention, a CT scanner includes a stationary gantry portion defining an examination region. A rotating gantry portion selectively rotates about the examination region. A plurality of anode elements, associated with the rotating gantry portion for selective bombardment by an electron stream, generate a plurality of parallel x-ray beams. Also included are a plurality of x-ray detectors receiving the x-ray beams which have passed through the examination region. The detectors generate signals indicative of the x-ray beams received and a reconstruction processor processes these generated signals into an image representation.

In accordance with another aspect of the present invention, the CT scanner further includes an x-ray tube body defining a vacuum envelope. The plurality of anode elements, each defining at least one target face, are disposed within the vacuum element.

In accordance with another aspect of the present invention, the CT scanner further includes a collimator externally adjacent to the body defining a series of alternating openings and septa. The openings have fan-shaped sides forming fan-shaped x-ray beams parallel to others of the x-ray beams and perpendicular to an axis through the examination region.

In accordance with another aspect of the present invention, the CT scanner further includes a plurality of x-ray tubes each including at least one of the anode elements. The x-ray tubes are spaced along an axis at a common angle relative to the examination region.

In accordance with another aspect of the present invention, the CT scanner includes a plurality of x-ray tubes, each comprising one of the anode elements where the x-ray tubes are spaced along an axis at a plurality of predefined angles relative to the examination region.

In accordance with the present invention, a method of diagnostic imaging includes simultaneously bombarding a plurality of axially spaced, parallel anode elements with electrons generating a plurality of x-ray beams. The x-ray beams are passed through an examination region where they are received and used to generate signals proportional to an amount of radiation received.

In accordance with another aspect of the present invention, the method of diagnostic imaging further includes receiving a desired imaging profile. A first set of anode elements to bombard for a first amount of time is determined based on the desired imaging profile received. A cathode assembly associated with each of the first set of anode elements is selectively powered for the first amount of time.

In accordance with the present invention, a method of diagnostic imaging includes concurrently generating a plurality of thin fan beams of penetrating radiation. The plurality of thin fan beams are passed through an examination region while the fan beams are concurrently rotating around the examination region. Each of the fan beams is detected after passing through the examination region and are used to generate electronic signals indicative of an amount of radiation which has passed through the examination region.

In accordance with another aspect of the present invention, the fan beams are rotated about an axis of rotation and the method further includes causing a relative axial movement along the axis of rotation between the examination region and the parallel fan beams.

In accordance with another aspect of the present invention, the method includes each of the parallel thin fan beams spaced equidistantly from each other wherein relative motion between the examination region and the parallel beams extend over a preselected distance such that each beam of radiation moves in a spiral pattern through a contiguous subvolume of the region of interest.

One advantage of the present invention resides in significantly improved imaging time as compared with conventional single fan beam CT systems.

Another advantage is that volumes can be imaged substantially in real time.

Another advantage of the present invention resides in the ability to use existing reconstruction algorithms to generate images.

Other benefits and advantages of the present invention will become apparent to those skilled in the art upon a reading and understanding of the preferred embodiments.

BRIEF DESCRIPTION OF THE DRAWINGS

The invention may take physical form in certain parts and arrangements of parts and in various steps and arrangements of steps. The drawings are only for purposes of illustrating the preferred embodiments and are not to be construed as limiting the invention.

DETAILED DESCRIPTION OF THE PREFERRED EMBODIMENT

Figure 1:
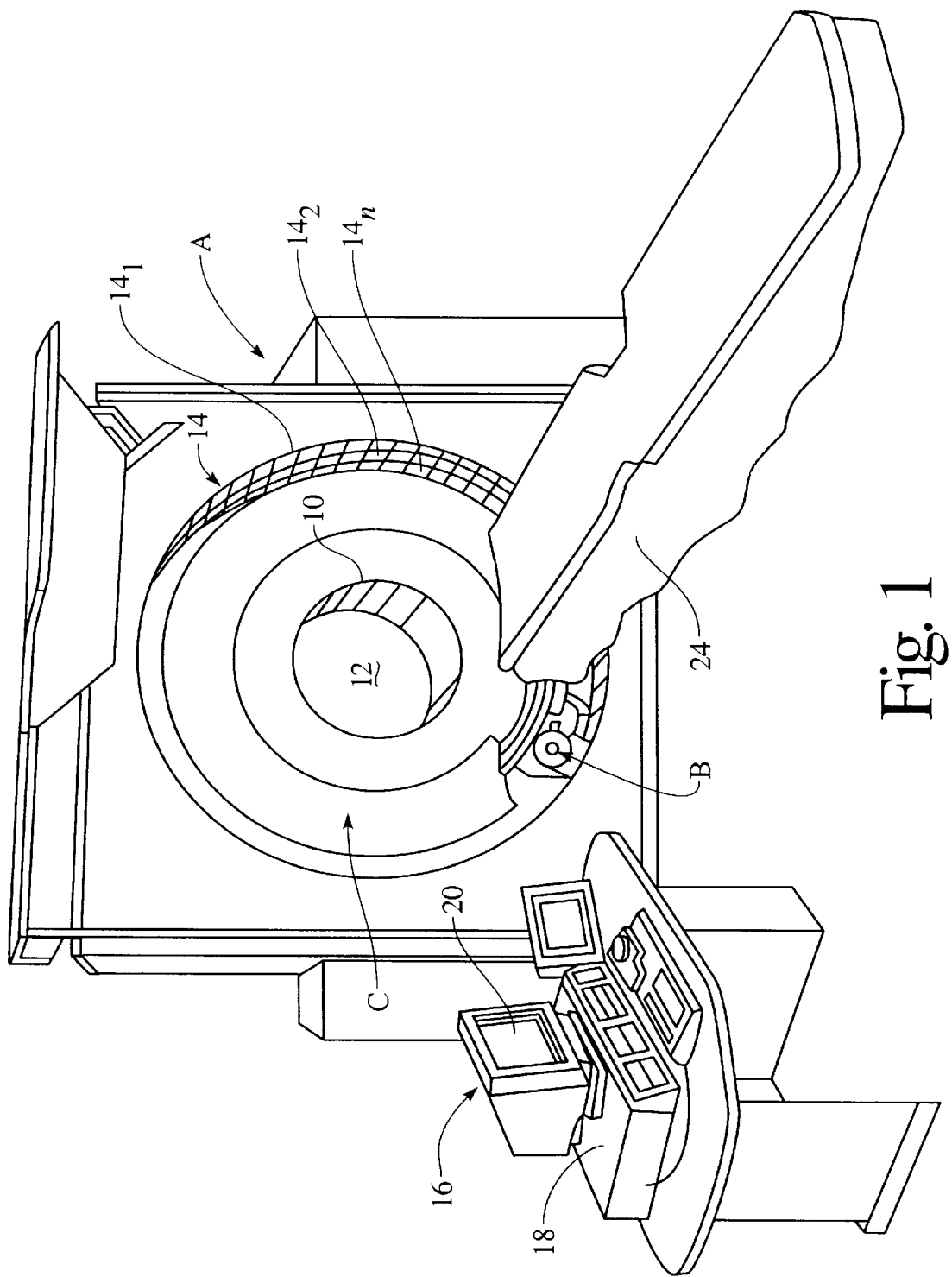
FIG. 1 is a perspective view of a continuous CT scanner system in accordance with the present invention.

With reference to FIG. 1, a CT scanner includes a floor mounted or stationary gantry A whose position remains fixed during data collection. A multiple fan beam generator B is rotatably mounted on a rotating gantry C. The stationary gantry A includes a cylinder 10 that defines a patient receiving region 12. A plurality of rings of radiation detectors $14_1, 14_2, \ldots 14_n$ are disposed concentrically around the patient receiving region 12. In the illustrated embodiment, the radiation detectors are mounted on the stationary gantry portion such that a corresponding arc segment of the detectors receives each fan beam of radiation from the radiation source B which has traversed a corresponding parallel path through the examination region 12. Alternately, a plurality of arc segments of radiation detectors can be mounted to the rotating gantry portion C each in alignment with one of the fan beams to rotate with the x-ray source.

A control console 16 contains an image reconstruction processor 18 for reconstructing a volumetric image representation using signals from the detector array $14_1, 14_2, \ldots 14_n$ for display on a monitor 20.

Figure 2:
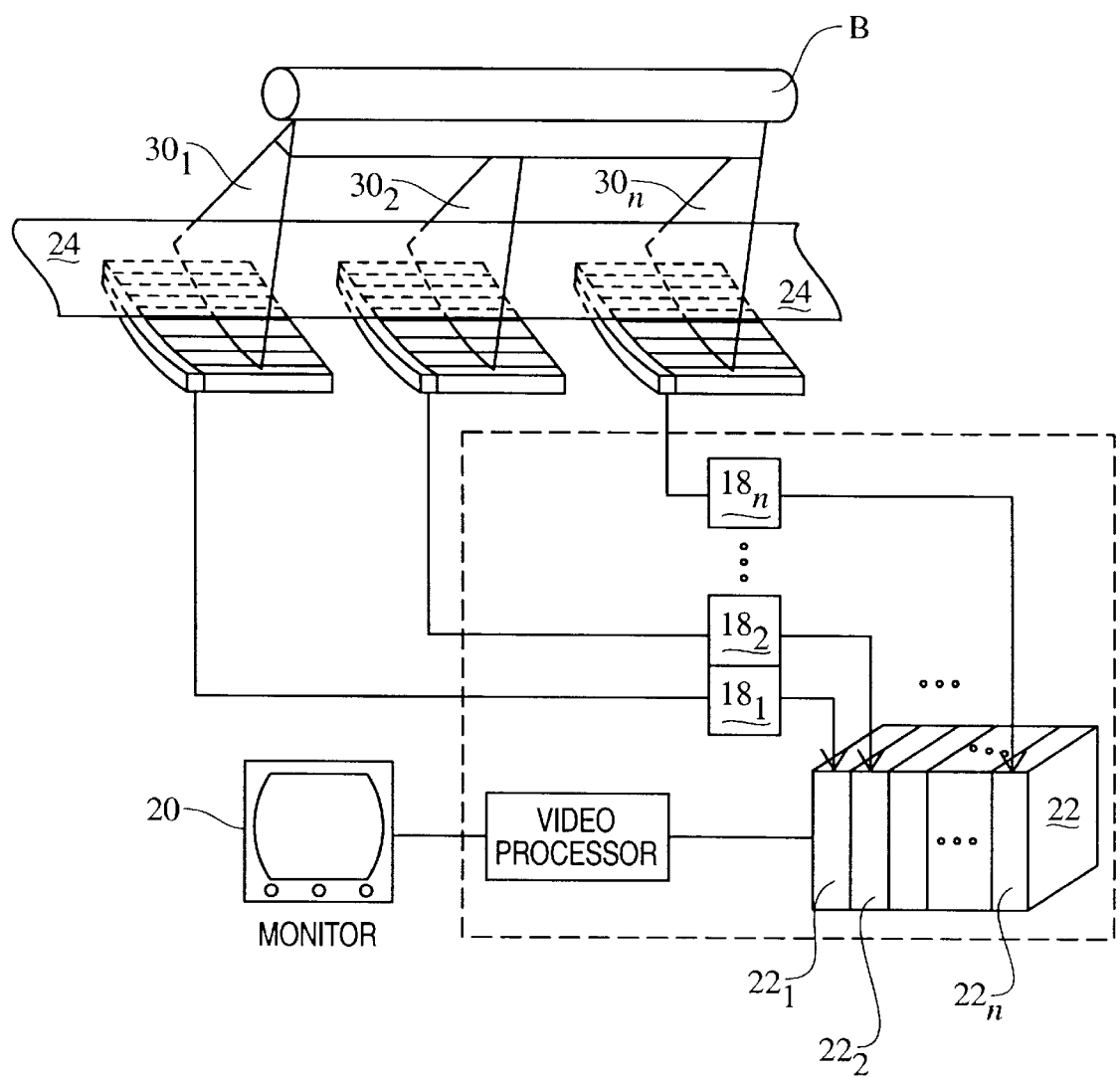
FIG. 2 is a diagrammatic illustration of a set of x-ray beams produced according to the present invention.

With reference to FIG. 2, in one embodiment the reconstruction processor 18 includes a plurality of reconstruction processors $18_1, 18_2, \ldots 18_n$, each preprogrammed using conventional slice image reconstruction algorithms. The output from each of the detector rings $14_1, 14_2, \ldots 14_n$ is fed to a corresponding processor $18_1, 18_2, \ldots 18_n$ which reconstructs the data collected concurrently into a series of slices. The series of slices is then stored in a volume image memory 22. If the x-ray beams are spaced immediately contiguous, then all of the slices of the volume image are reconstructed concurrently. However, in the preferred embodiment, the number of slices is less than the total number of slices in the volume and the slices are spread apart such that some fraction of the slices, e.g. every sixth slices, are generated concurrently. Thereafter, a patient couch 24 is stepped one slice distance and the next set of slices is generated concurrently. In the present example in which one sixth of the slices is taken each time, this process is repeated six times.

In another preferred embodiment, the slices are again spaced by some short distance. The patient table 24 moves in either direction through the imaging area or back and forth continuously as the x-ray beams rotate continuously. The motion of the patient table is selected such that the data collected by each of the radiation detectors spirals in each of a plurality of contiguous slabs. The data in each of the slabs is reconstructed, preferably concurrently by a plurality of parallel processors, using conventional spiral volume imaging algorithms.

In yet another alternate embodiment, the patient table moves back and forth a sufficient distance that the spirals overlap. The conventional spiral imaging algorithm is modified such that each of a series of preferably parallel processors is updating a corresponding region of volume image memory 22, concurrently.

The video monitor 20 converts selectable portions of the reconstructed volumetric image representation into a two-dimensional human-readable display. The console 16 also includes appropriate tape or disk recording devices, performing image enhancements, selecting planes for viewing, 3-D renderings, or color enhancements or the like. Various scanner control functions such as initiating a scan, selecting among different types of scans, calibrating the system and the like are also performed at the control console.

With reference to FIGS. 1 and 2, the x-ray generator B is elongated along an axis parallel to the examination region 12. Multiple parallel fan-shaped beams $30_1, 30_2, \ldots 30_n$ are simultaneously produced. In the illustrated embodiment, both the generator B and the detector $14_1, 14_2, \ldots 14_n$ are mounted to the rotating gantry C. Preferably, the rotating gantry C rotates the apexes of the beams $30_1, 30_2, \ldots 30_n$ about the examination region 12 and radiation data is collected by the detectors 14. Volume scans are achieved by axially moving the couch 24 or region of interest through the examination region 12 and the plurality of x-ray beams $30_1, 30_2, \ldots 30_n$. Those skilled in the art can appreciate that any number of x-ray beams may be generated, and that the time required for a volume scan or coverage time is reduced by a factor proportional to the number of x-ray beams used.

Figure 3:
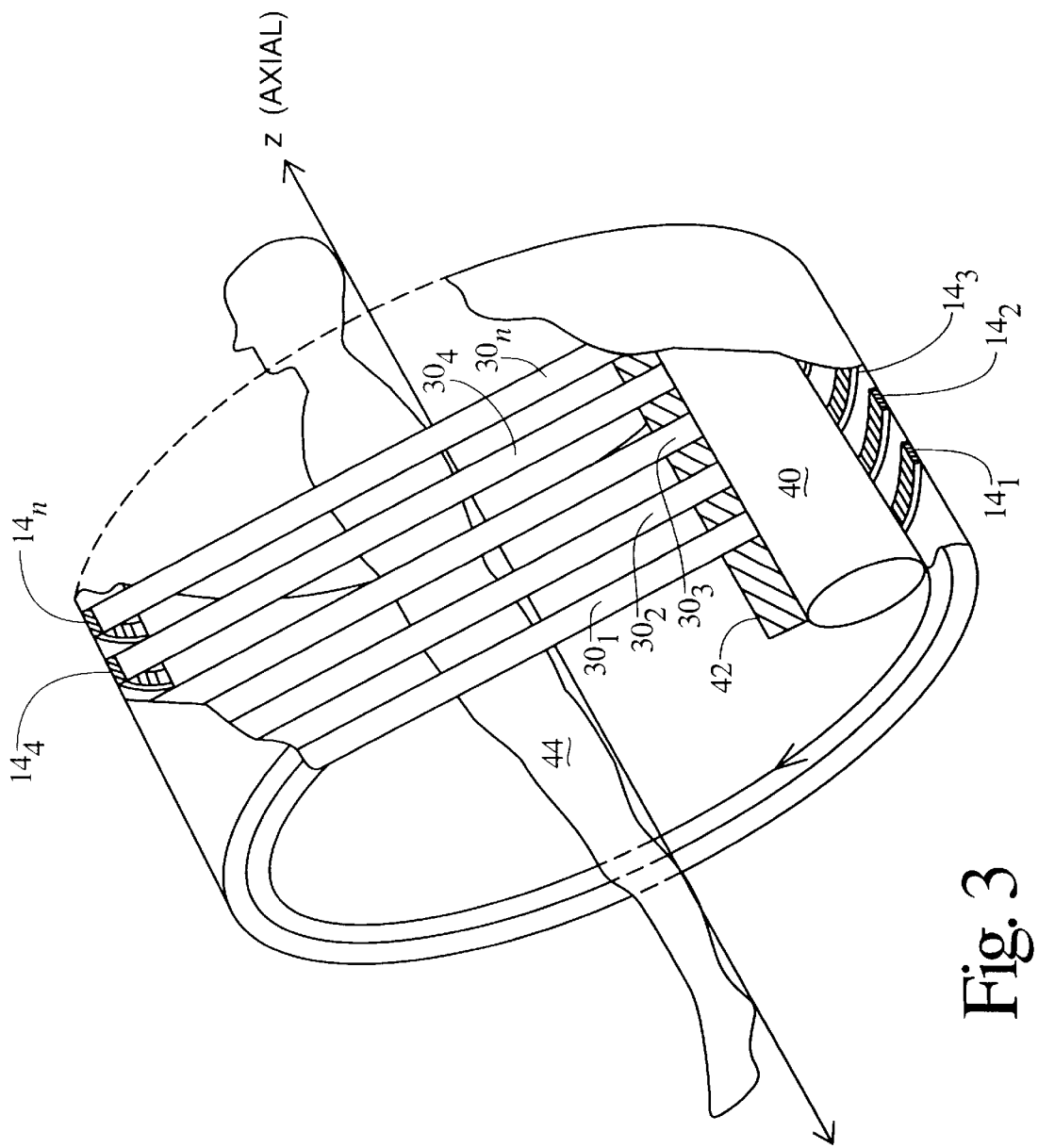
FIG. 3 is a detail of a fourth generation CT scanner in accordance with the present invention.

FIG. 3 depicts a single elongated x-ray tube 40 capable of generating n parallel fan-shaped x-ray beams $30_1, 30_2, \ldots 30_n$. The beams $30_1, 30_2, \ldots 30_n$ are generated and collimated by a collimator 42. The collimator 42 is disposed adjacent to the x-ray beam source and channels the beams $30_1, 30_2, \ldots 30_n$ into a series of parallel axially spaced fan-shaped rays. The beams are attenuated as they pass through a subject 44 and are received by the plurality of axially spaced detector arrays $14_1, 14_2, \ldots 14_n$. The detector arrays $14_1, 14_2, \ldots 14_n$ generate electrical signals each proportional to the radiation received along a corresponding ray of each fan as is known in the art. Alternately, the detector arrays could be configured as semi-circular arcs sufficient to receive the x-ray beam arc and could further be rotatably mounted to the rotating gantry portion in a third generation scanner (as shown in FIG. 2).

Figure 4:
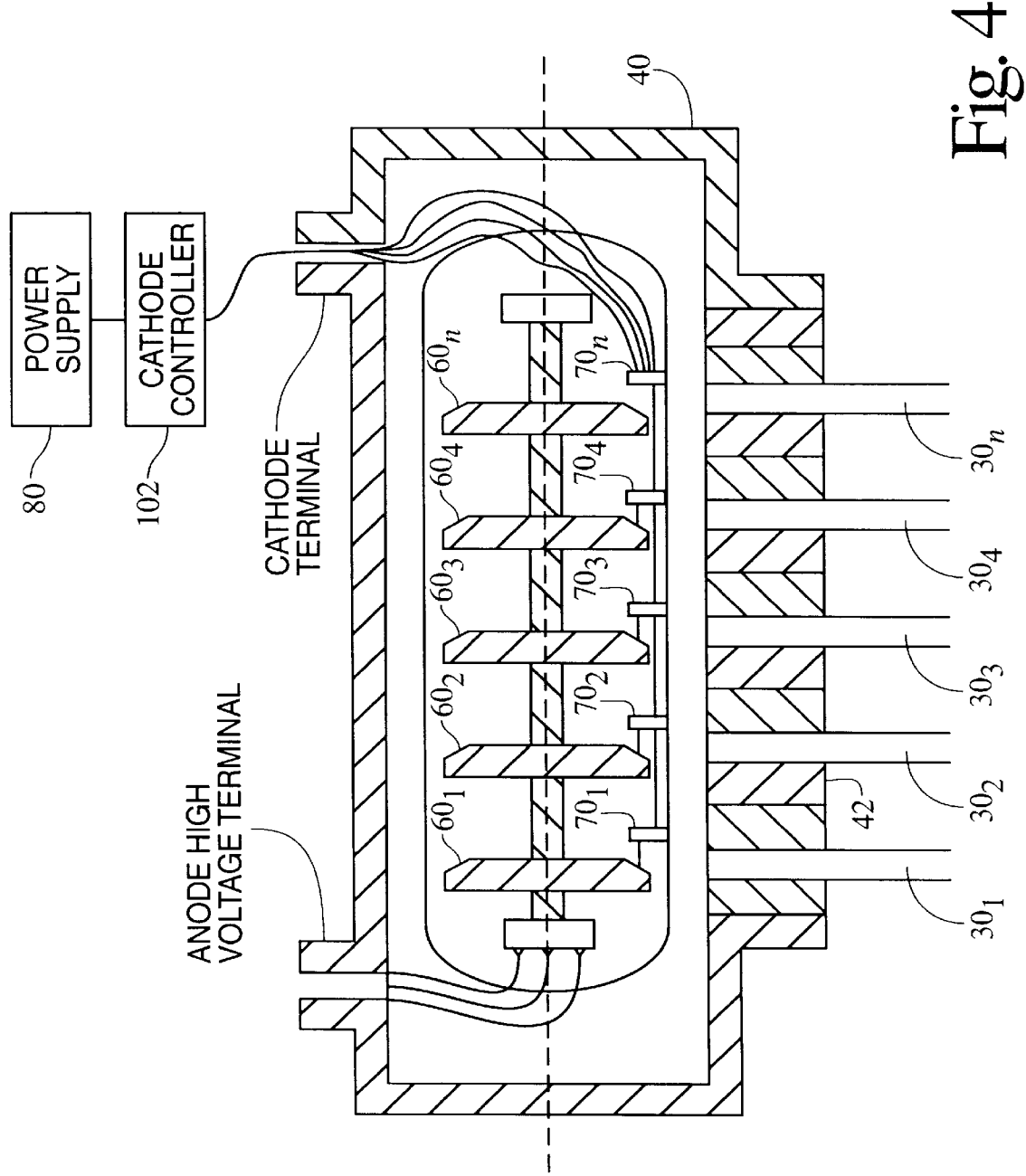
FIG. 4 is a cross-section of a multiple anode x-ray tube suitable to meet the present invention.

Cross-referencing FIG. 3 and FIG. 4, the axially elongated x-ray tube 40 houses a plurality of rotating anode elements $60_1, 60_2, \ldots 60_n$. Each anode element $60_1, 60_2, \ldots 60_n$ is associated with a cathode assembly $70_1, 70_2, \ldots 70_n$, selectably excitable by a filament power supply 80. When selected, each cathode assembly generates an electron stream which strikes the corresponding anode element and produces x-ray beams. The x-ray beams are collimated by the collimator 42 into the plurality of parallel axially spaced x-ray beams $30_1, 30_2, \ldots 30_n$.

Figure 5:
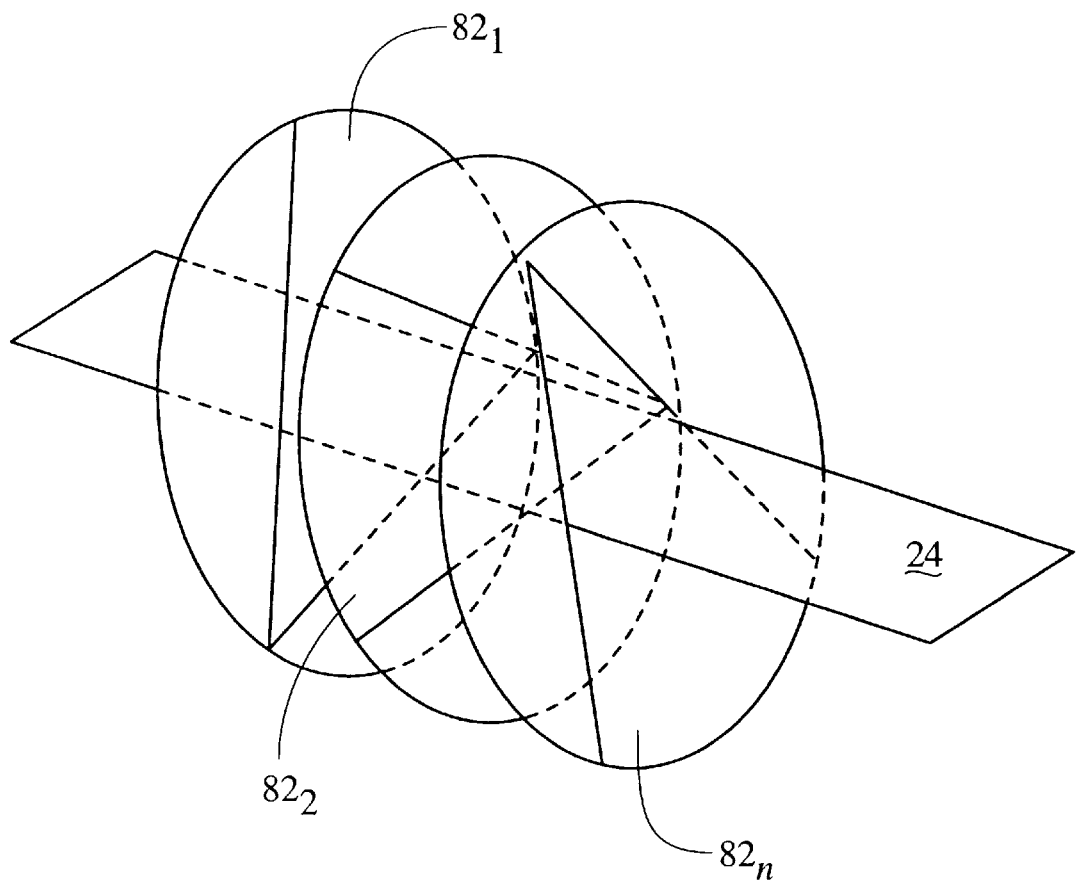
FIG. 5 is a diagrammatic illustration of an alternate set of x-ray beams produced in accordance with the present invention.

Alternatively, as seen in FIG. 5, the radiation source generates axially spaced parallel x-ray beams $82_1, 82_2, \ldots 82_n$ that are angularly spaced from one another with respect to the examination region 12. In one embodiment, a plurality of x-ray tubes $90_1, 90_2, \ldots 90_n$ are mounted onto the rotating gantry C as may be appreciated by reference to FIG. 6. In a preferred embodiment in which n=3, the x-ray sources are evenly angularly separated at 120° intervals about the examination region 12, but may be spaced at any offset angle. The fan beams $82_1, 82_2, 82_3$ are received by the detector array 14 in specific, isolated areas $84_1, 84_2, 84_3$.

Figures 6, 7:
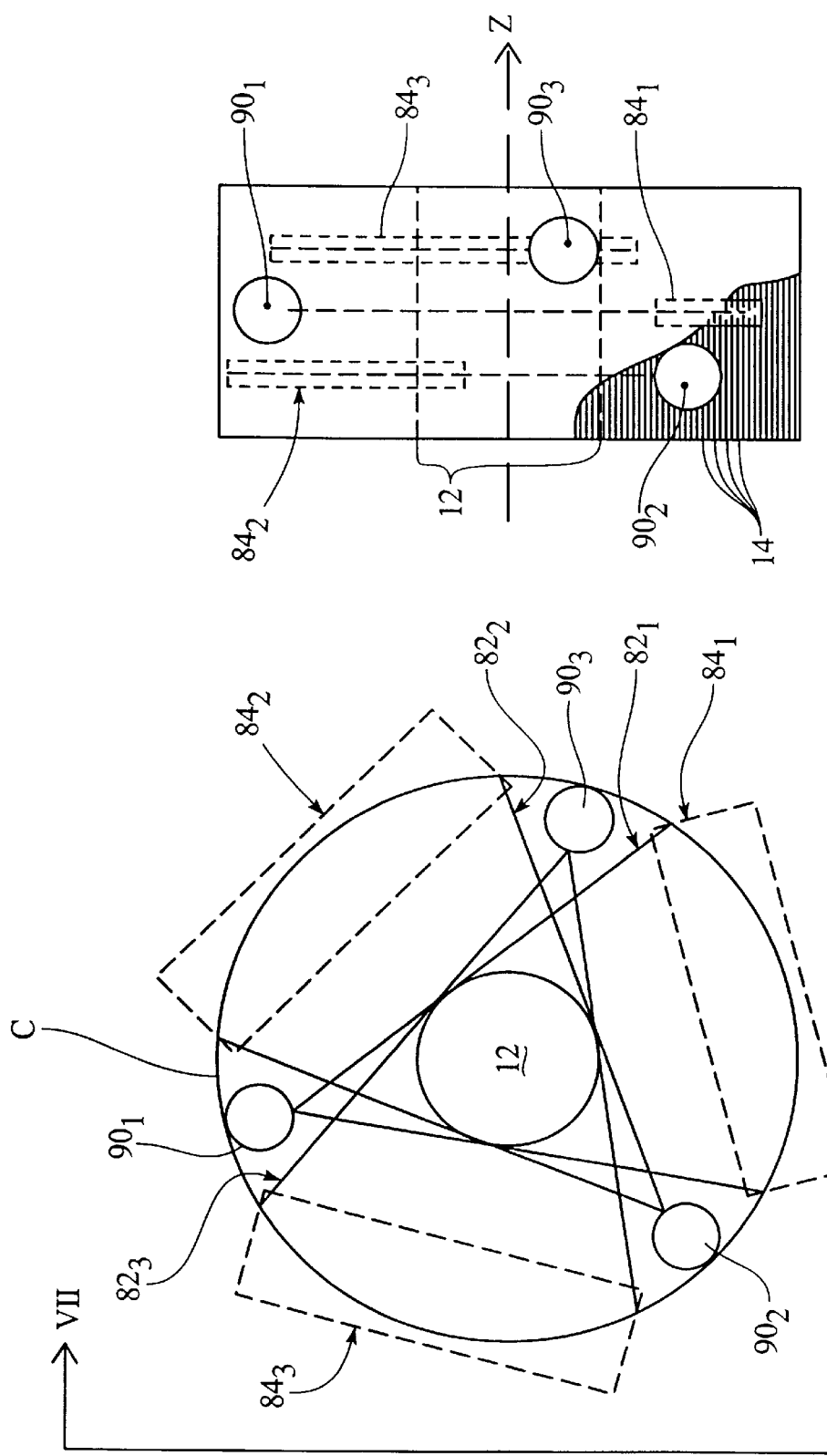
FIG. 6 is a detail of an alternate embodiment of a fourth generation scanner according to the present invention.
FIG. 7 is a cross-section of the scanner from FIG. 6.

FIG. 7 depicts a cross-section of the CT scanner of FIG. 6 to depict more clearly the axial separation of the x-ray tubes $90_1, 90_2, 90_3$. In the illustrated embodiment, a single substantially continuous detector array 14 is mounted to the stationary gantry portion A to receive the x-ray beams generated by the x-ray tubes $90_1, 90_2, 90_3$. The x-ray beams $82_1, 82_2, 82_3$ are closely collimated to strike the single detector array 14 in locations angularly displaced from one another. Moreover, because the x-ray tubes are angularly spaced about the examination region 12, each x-ray beam $82_1, 82_2, 82_3$ is received by the detector array 14 over a unique arc $84_1, 84_2, 84_3$. In other words, the x-ray beams $82_1, 82_2, 82_3$ do not overlap, so that the single detector array 14 can produce signals representative of the three separate beams.

In another alternate embodiment, a plurality of multiple anode element tubes, such as are illustrated by reference number 40 in FIG. 4, are mounted in intervals around a plurality of rings of radiation detectors $14_1, 14_2, \ldots 14_n$ as illustrated in FIG. 3. Again, the x-ray sources are spaced an appropriate distance such that each fan beam irradiates a unique arc segment of one of the rings. For example, three of the x-ray sources can be disposed about 120° apart around the examination region. As yet another option, a larger number of multiple anode x-ray tubes may be positioned around the subject and the various anodes gated on and off to prevent more than one beam from irradiating a common detector element of one of the rings.

Figure 8:
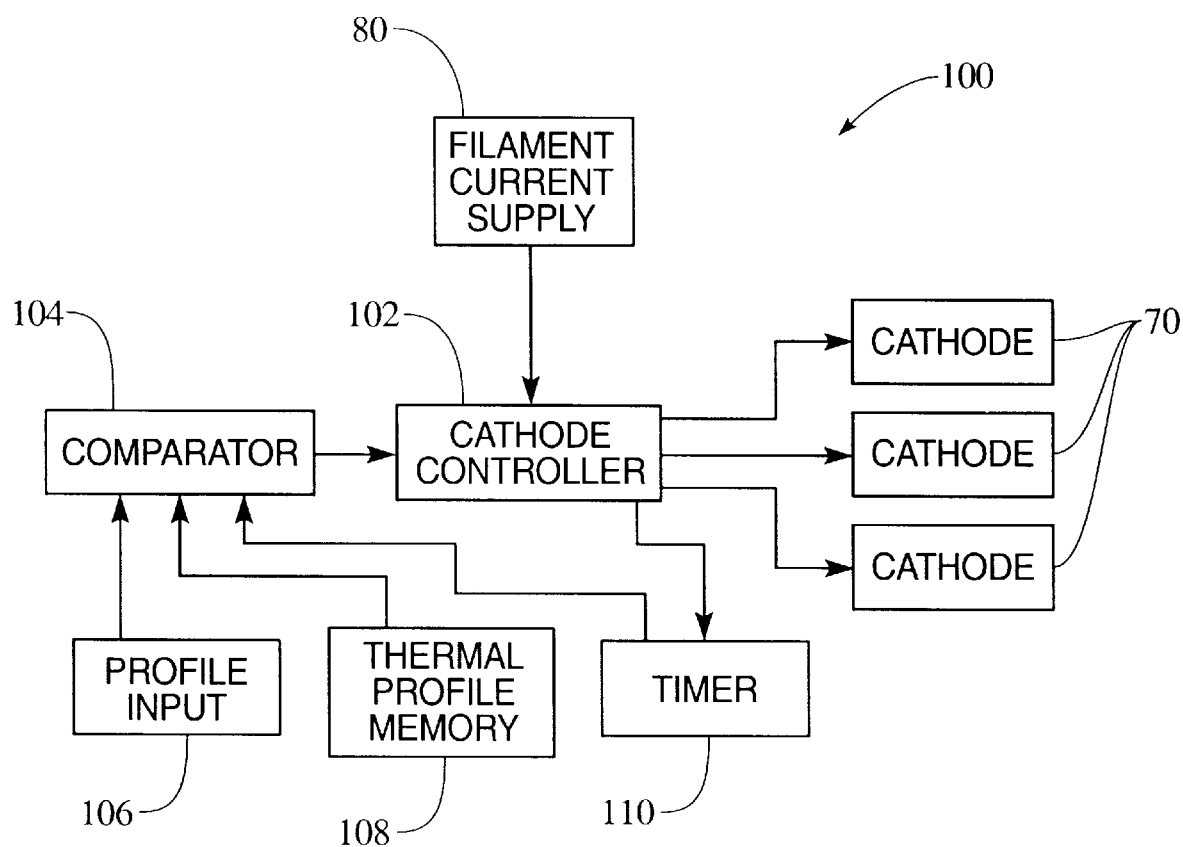
FIG. 8 is a block diagram of an exemplary control circuit suitable to practice the present invention.

Referring now to FIG. 8 the x-ray tube assembly preferably includes a control circuit 100 for selectively powering the cathode assemblies 70. A cathode controller 102 is electrically connected between the filament current supply 80 and the individual cathode assemblies 70. The cathode controller 102 can be configured as a grid control tube, electrical switch circuit, or the like. A comparator 104 controls the cathode controller 102 based on selected inputs. Preferably the selected inputs include a profile input 106, a thermal profile memory or look up table 108, and a timer 110. The profile input 106 is preferably an input source where a technician can select a desired imaging pattern based on diagnostic needs. For example, the profile input desired may be for all multiple fan beams to be used simultaneously providing a maximum number of image slices in the shortest time. On the other hand, the desired profile may be to alternate or cycle selected sub-sets of multiple fan beams, perhaps to cover a larger volume.

As a further example, the technician may desire a maximum number of slices within the temperature envelope of the x-ray tube assembly. In this event, the thermal profile memory 108 is accessed to estimate the time that the anode elements can be bombarded with electrons before a period of rest, or non-use must occur to facilitate removal of excess thermal energy. The memory 108 is preloaded with thermal curves specific to the anode elements of the tube. Then, when the tubes are powered, a timer 110 calculates the amount of time the individual cathodes have been on. This time allows the comparator to estimate thermal loading conditions of the anode elements in use by plotting the time onto the thermal profile memory.

Regardless of profile desired, the comparator 104 receives the inputs, determines the sequence of operation and controls the cathode controller 102 to individually select specific cathode assemblies 70.

The invention has been described with reference to the preferred embodiments. Potential modifications and alterations will occur to others upon a reading and understanding of the specification. It is our intention to include all such modifications and alterations insofar as they come within the scope of the appended claims, or the equivalents thereof.

Having thus described the preferred embodiments, the invention is now claimed to be:

1. A CT scanner comprising:
a rotating gantry portion selectively rotating about an examination region;
an x-ray tube body defining a vacuum envelope, mounted to the rotating gantry portion;
a plurality of discrete anodes mounted within the vacuum envelope, the anodes selectively generating a plurality of parallel x-ray beams;
a plurality of x-ray detectors receiving the x-ray beams which have passed through the examination region and generating signals indicative of the x-ray beams received; and
a reconstruction processor processing the generated signals into an image representation.

2. The CT scanner as set forth in claim 1, further including:
a plurality of cathode assemblies mounted within the vacuum envelope.

3. The CT scanner as set forth in claim 1, further including:
a collimator externally adjacent to the body defining a series of alternating openings and septa, the openings having fan-shaped sides forming fan-shaped x-ray beams parallel to others of the x-ray beams and perpendicular to an axis through the examination region.

4. The CT scanner as set forth in claim 2 further including:
means for selectively switching on and off the electron stream between any of the cathode assemblies and an associated target face.

5. The CT scanner as set forth in claim 1, further including:
a second x-ray tube body defining a vacuum envelope with a second plurality of discrete anodes and a second plurality of cathode assemblies disposed within, each x-ray tube being mounted to the rotating gantry portion, and spaced along an axis at a common angle relative to the examination region; and a plurality of collimators each externally adjacent to one of the x-ray tubes, where the collimators define an opening having fan-shaped sides forming parallel fan-shaped x-ray beams.

6. The CT scanner as set forth in claim 1, further including:

a second x-ray tube body defining a vacuum envelope with a second plurality of discrete anodes and a second plurality of cathode assemblies disposed within, wherein each x-ray tube is mounted to the rotating gantry portion at a plurality of predefined angles relative to the examination region; and a collimator externally adjacent to each of the x-ray tubes, where the collimator defines an opening having fan-shaped sides forming parallel fan-shaped x-ray beams.

7. The CT scanner as set forth in claim 1 wherein the plurality of x-ray detectors include a substantially continuous ring of detector elements mounted to the stationary gantry portion.

8. The CT scanner as set forth in claim 1 wherein the plurality of x-ray detectors comprise a set of axially spaced continuous rings of detector elements mounted to the stationary gantry portion.

9. The CT scanner as set forth in claim 1 wherein the plurality of x-ray detectors comprise axially spaced arcs of detector elements mounted to the rotating gantry portion, each arc opposite an apex of the x-ray beams.

10. A method of diagnostic imaging comprising:

spacing a plurality of discrete anodes such that a focal spot on each anode is aligned on an axis parallel to a longitudinal axis through an examination region;

bombarding selected anodes with electrons generating a plurality of x-ray beams spaced along the longitudinal axis;

receiving the x-ray beams and generating signals proportional to an amount of radiation received; and reconstructing the signals into an image representation.

11. The method of diagnostic imaging as set forth in claim 10, further including:

rotating the anodes about the examination region; and inducing relative motion along the longitudinal axis.

12. The method of diagnostic imaging as set forth in claim 11, wherein the bombarding step includes:

receiving a desired imaging profile;

determining a first set of anodes to bombard for a first time based on the desired imaging profile received; and selectively powering a cathode assembly associated with each of the first set of anodes for the first time.

13. A method of diagnostic imaging including:

spacing a plurality of anode element focal spots on an axis parallel to a longitudinal axis through an examination region;

determining a first set of anode element focal spots to bombard for a first time based on a received imaging profile;

powering selected cathode assemblies to concurrently bombard the first set of anode element focal spots;

determining a second set of anode element focal spots to bombard for a second time based on the received imaging profile; and after the first time, powering selected cathode assemblies to concurrently bombard the second set of anode element focal spots.

14. The method of diagnostic imaging as set forth in claim 13 further including collimating generated x-ray beams into thin, parallel fans, which parallel fans are passed through the examination region.

15. A method of diagnostic imaging comprising:

concurrently generating a plurality of thin fan beams of penetrating radiation, each fan beam having an apex along a common line parallel to a longitudinal axis through an examination region;

passing the plurality of thin fan beams of penetrating radiation through the examination region and concurrently rotating the apex of the fan beams around the examination region;

detecting each of the fan beams of radiation after it has passed through the examination region and generating electronic signals indicative of an amount of radiation which passed through the examination region; and reconstructing electronic signals into a volumetric image representation.

16. The method as set forth in claim 15, further including:

causing relative axial movement along the longitudinal axis between the examination region and the parallel fan beams of radiation.

17. The method as set forth in claim 16, wherein the examination region and the parallel fan shaped beams of radiation are moved in steps and after each step, the received electronic signals representative of the fan shaped beams are reconstructed into an imaging representation of a parallel slice, such that slices of the volumetric image representation are collected a plurality of parallel, spaced slices at a time.

18. The method as set forth in claim 15, wherein the thin fan beams of radiation are parallel to others of the thin fan beams, the method further including:

continuously moving the examination region and the parallel thin fan beams of radiation along the longitudinal axis such that each of the parallel beams of radiation traverse a spiral through the examination region.

19. The method as set forth in claim 18 wherein the parallel thin fan beams of radiation are separated by a common distance and wherein relative motion between the examination region and the parallel beams of radiation is greater than a preselected distance such that the parallel beams of radiation traverse spiral paths, which spiral paths at least partially overlap.

20. The method as set forth in claim 19 wherein each of the parallel thin fan beams of radiation are spaced equidistantly from each other and wherein relative motion between the examination region and the parallel beams extends over a preselected distance such that each beam of radiation moves in a spiral pattern through a contiguous subvolume of the examination region.

* * * * *